US012800565B2

(12) United States Patent
Baret

(10) Patent No.: US 12,800,565 B2
(45) Date of Patent: Nov. 17, 2026

(54) DEVICE FOR ANALYSING A LIQUID MEDIUM, IN PARTICULAR SWIMMING POOL WATER

(71) Applicant: BLEU ELECTRIQUE, Marseilles (FR)

(72) Inventor: Emmanuel Baret, Marseilles (FR)

( * ) Notice: Subject to any disclaimer, the term of this patent is extended or adjusted under 35 U.S.C. 154(b) by 359 days.

(21) Appl. No.: 18/693,011

(22) PCT Filed: Sep. 13, 2022

(86) PCT No.: PCT/IB2022/058616
§ 371 (c)(1),
(2) Date: Mar. 18, 2024

(87) PCT Pub. No.: WO2023/042071
PCT Pub. Date: Mar. 23, 2023

(65) Prior Publication Data

US 2025/0003943 A1 Jan. 2, 2025

(30) Foreign Application Priority Data

Sep. 17, 2021 (FR) ...................................... 2109763

(51) Int. Cl.
*G01N 33/18* (2006.01)
*E04H 4/08* (2006.01)
*E04H 4/14* (2006.01)

(52) U.S. Cl.
CPC ......... *G01N 33/1886* (2013.01); *E04H 4/082* (2013.01); *E04H 4/14* (2013.01)

(58) Field of Classification Search
CPC .................................................. G01N 33/1886
See application file for complete search history.

(56) References Cited

U.S. PATENT DOCUMENTS 11,345,611 B2 * 5/2022 Burnham ................ E04H 4/148
2014/0007338 A1 1/2014 Shpringer
(Continued)

FOREIGN PATENT DOCUMENTS

FR 3064360 A1 9/2018
WO WO-2019186186 A1 * 10/2019 ............ E04H 4/103

OTHER PUBLICATIONS

International Search Report for corresponding PCT/IB2022/058616 dated Dec. 12, 2022.
(Continued)

*Primary Examiner* — Suman K Nath
*Assistant Examiner* — Alex T Devito
(74) *Attorney, Agent, or Firm* — Egbert, McDaniel & Swartz, PLLC

(57) ABSTRACT

Disclosed is a device for analysing a liquid medium having a casing housing for analysing the liquid medium in order to measure the physico-chemical parameters of the liquid medium, a monitor to manage the measured parameters, a communication mechanism capable of transmitting the parameters to a central unit, at least one photovoltaic panel in connection with an electrical energy storage for supplying electrical power to an analyzer, monitor and the communication mechanism. The casing includes a gripping member arranged in a U-shape, which defines a space capable of receiving one end of a protective flap and provided with a mechanism for detecting the position of the protective flap inside the space.

9 Claims, 13 Drawing Sheets

(56) References Cited

U.S. PATENT DOCUMENTS

2019/0108745 A1 4/2019 Tepper
2019/0136557 A1* 5/2019 Jensen .................. E04H 4/1272
2019/0257807 A1* 8/2019 Witelson ................. B63B 35/00

OTHER PUBLICATIONS

Written Opinion of the International Searching Authority for corresponding PCT/IB2022/058616 dated Dec. 12, 2022.

* cited by examiner

[Fig. 1]
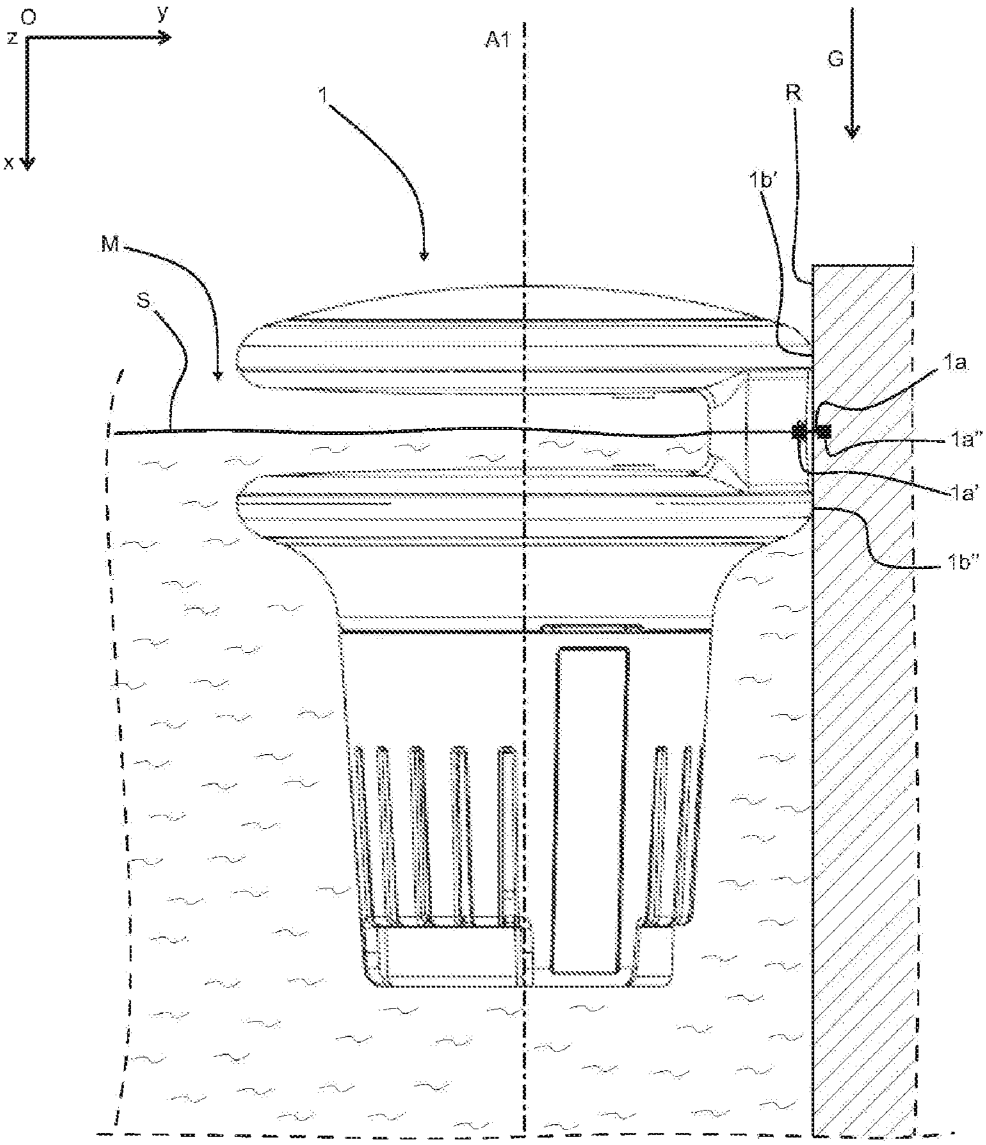

[Fig. 2]
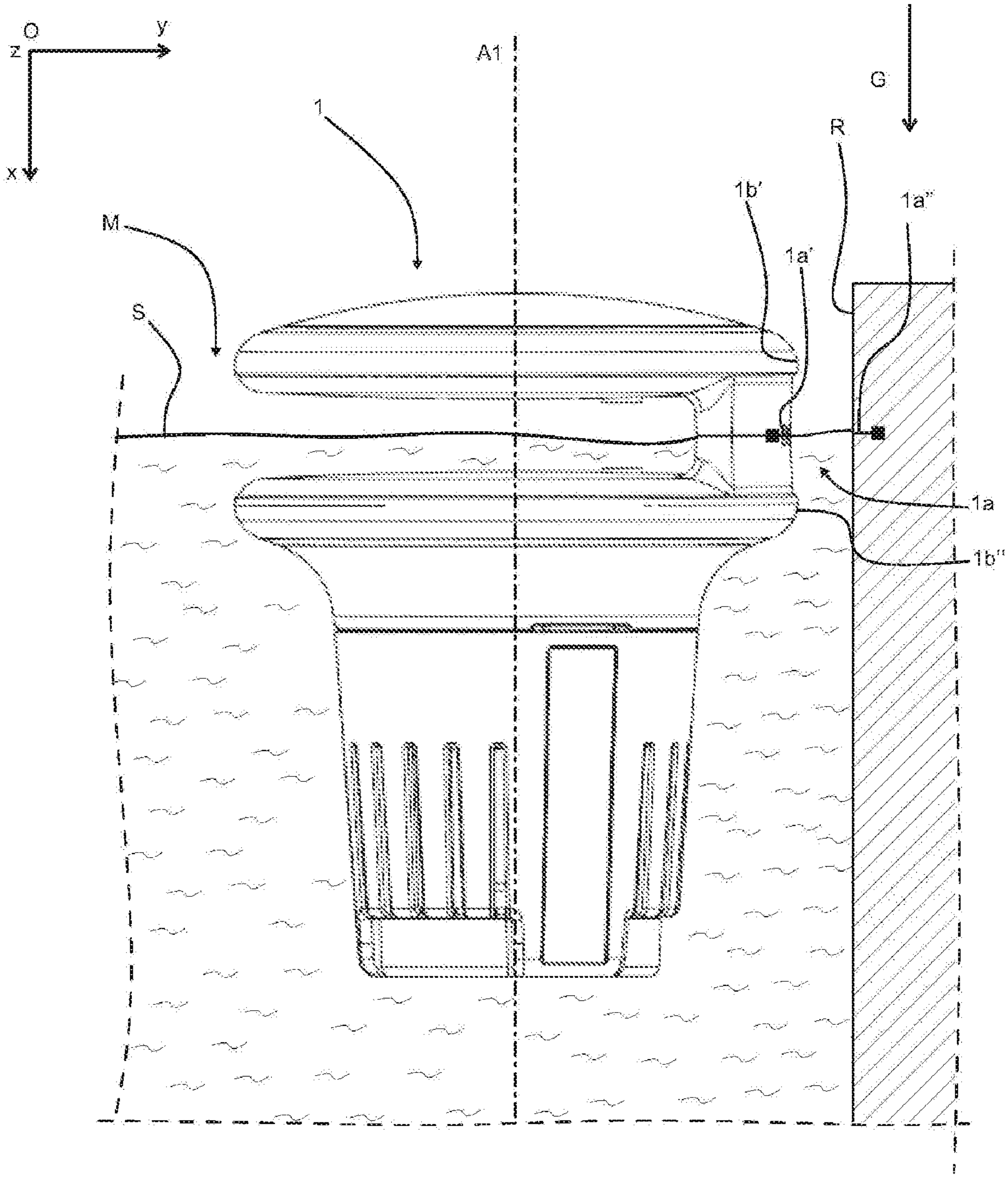

[Fig. 3]
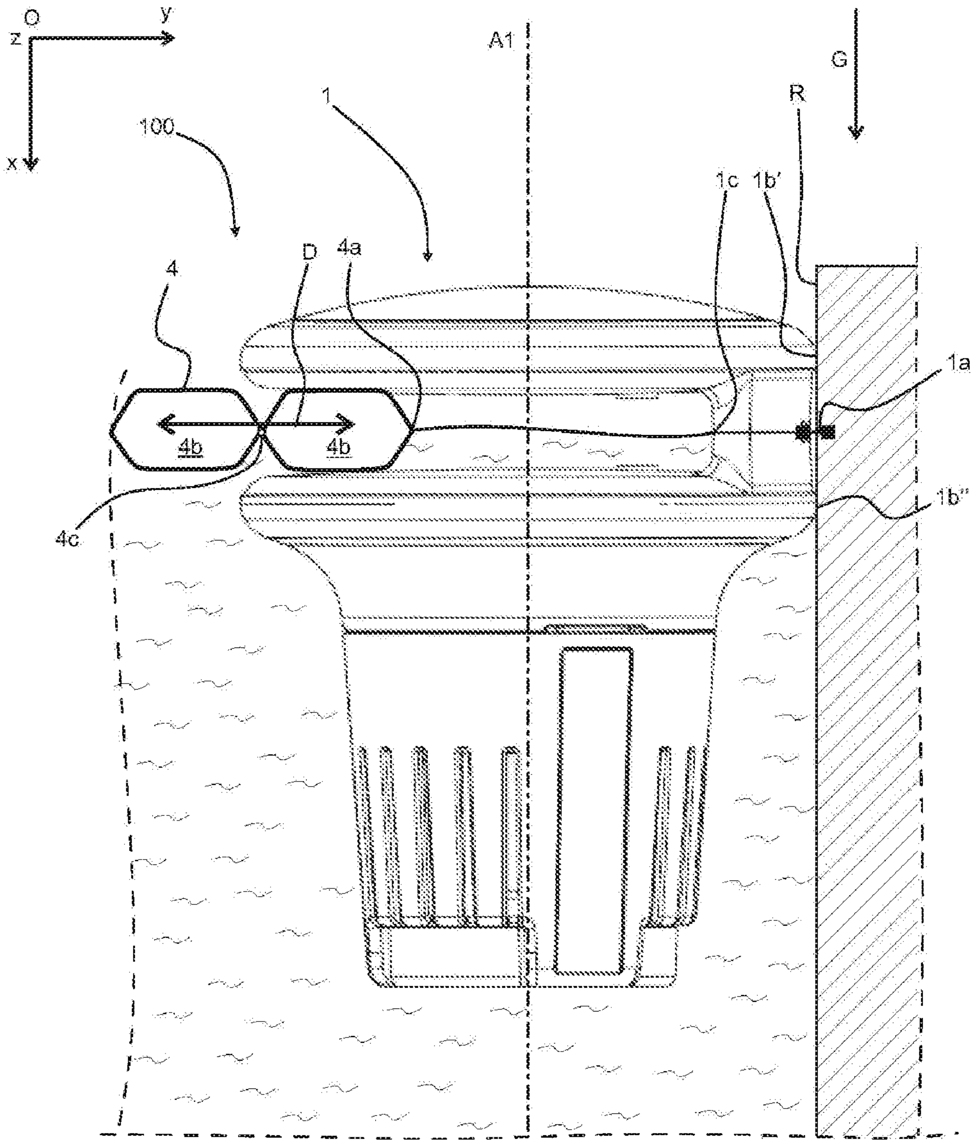

[Fig. 4]
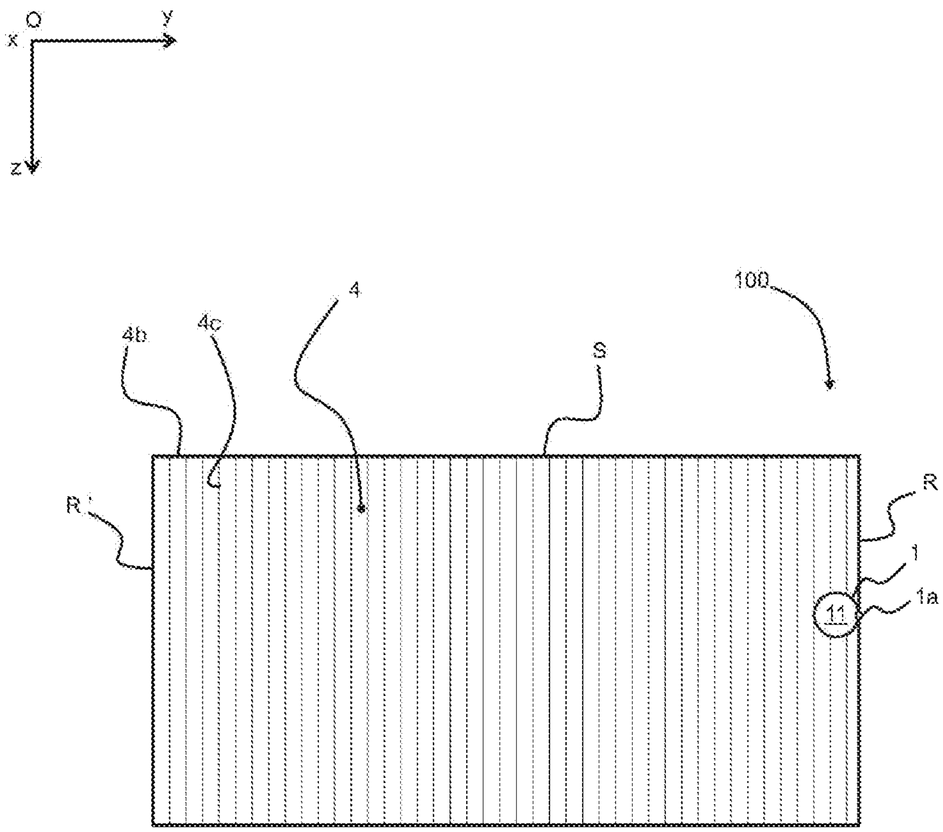

[Fig. 5]
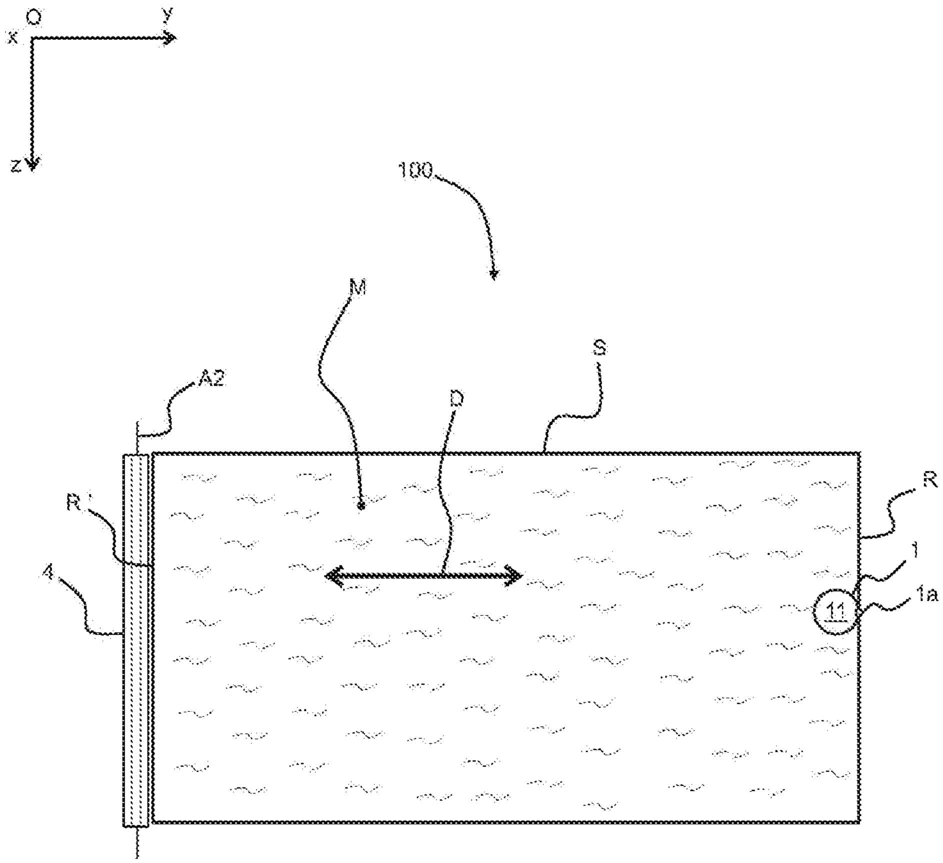

[Fig. 6]
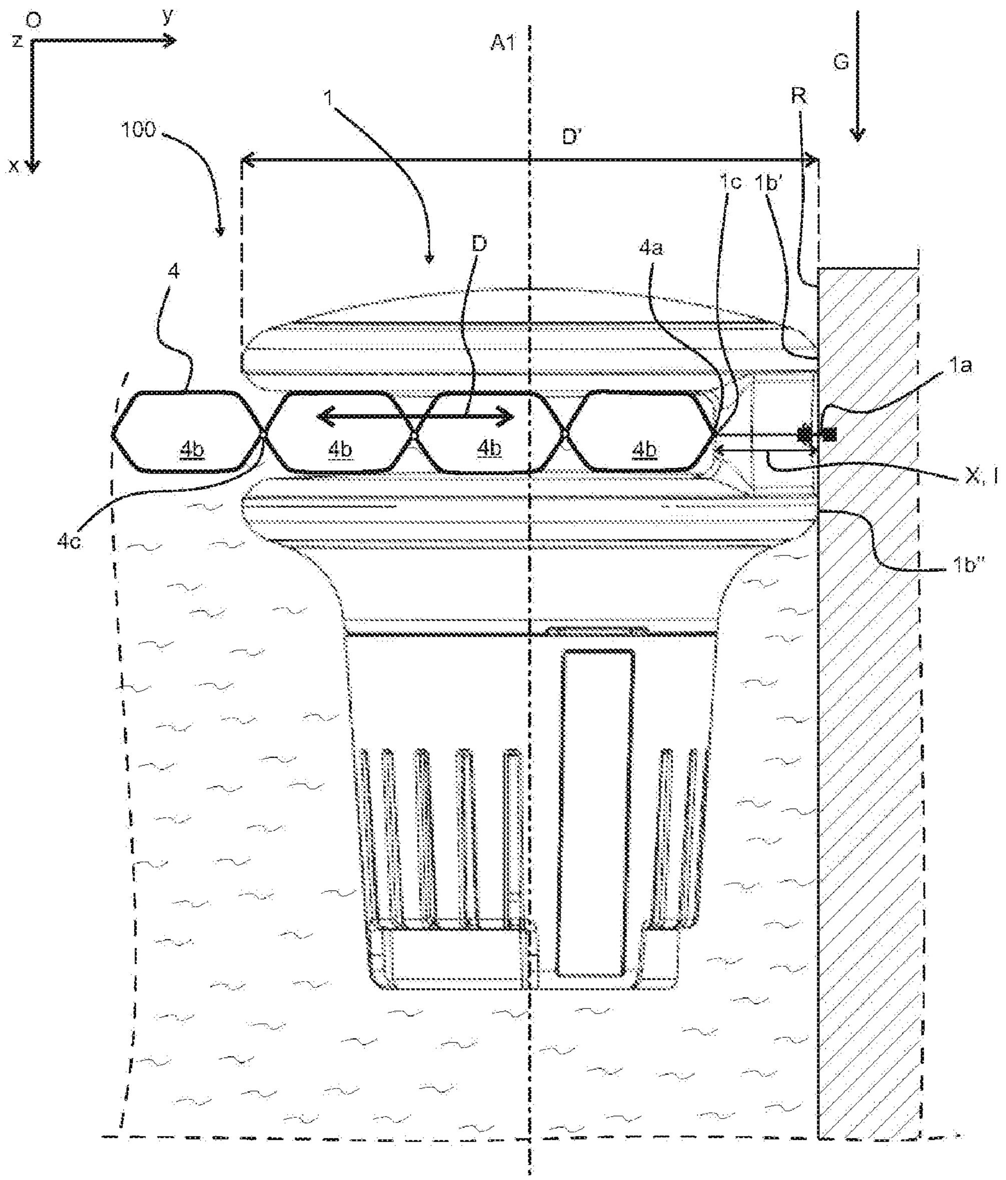

[Fig. 7]
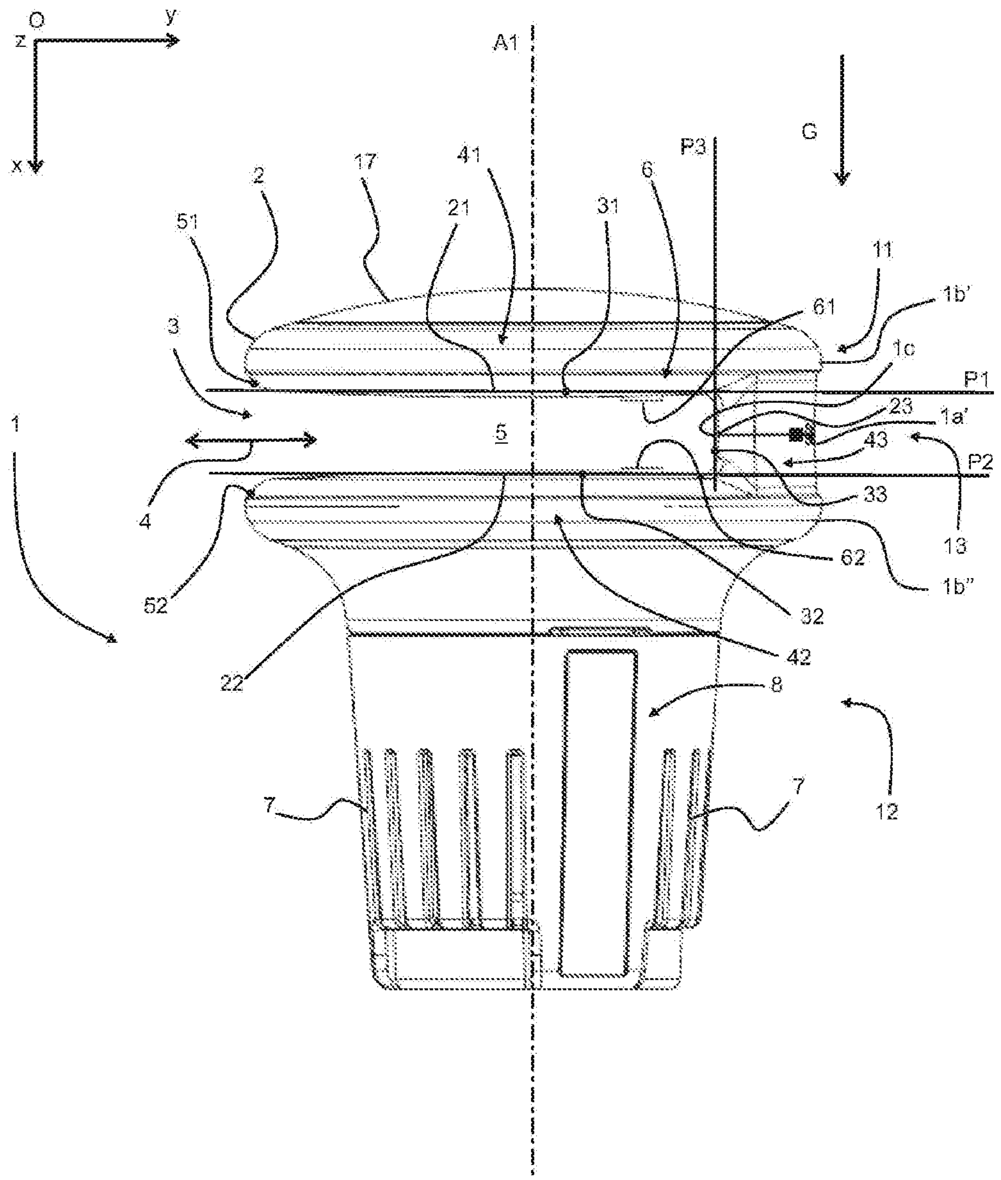

[Fig. 8]
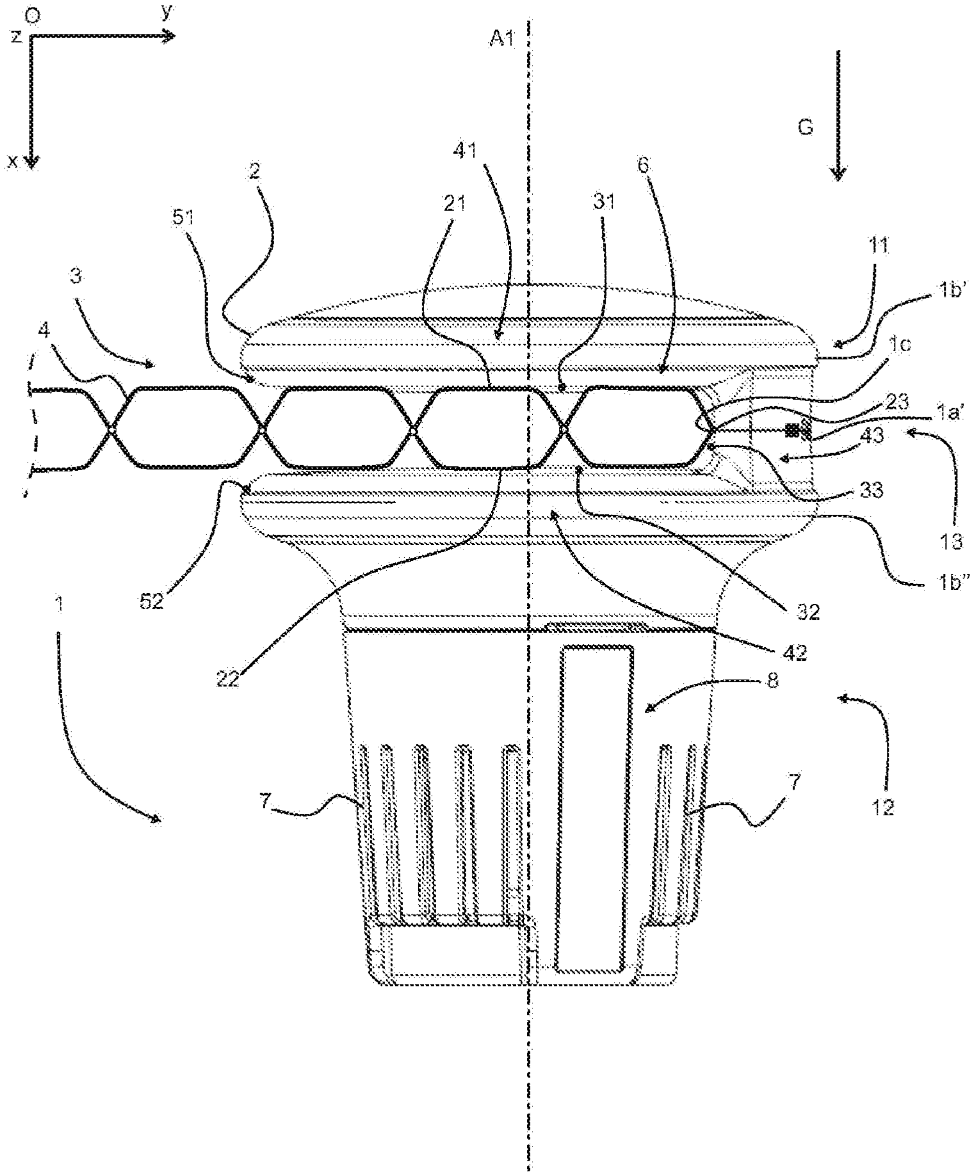

[Fig. 9]
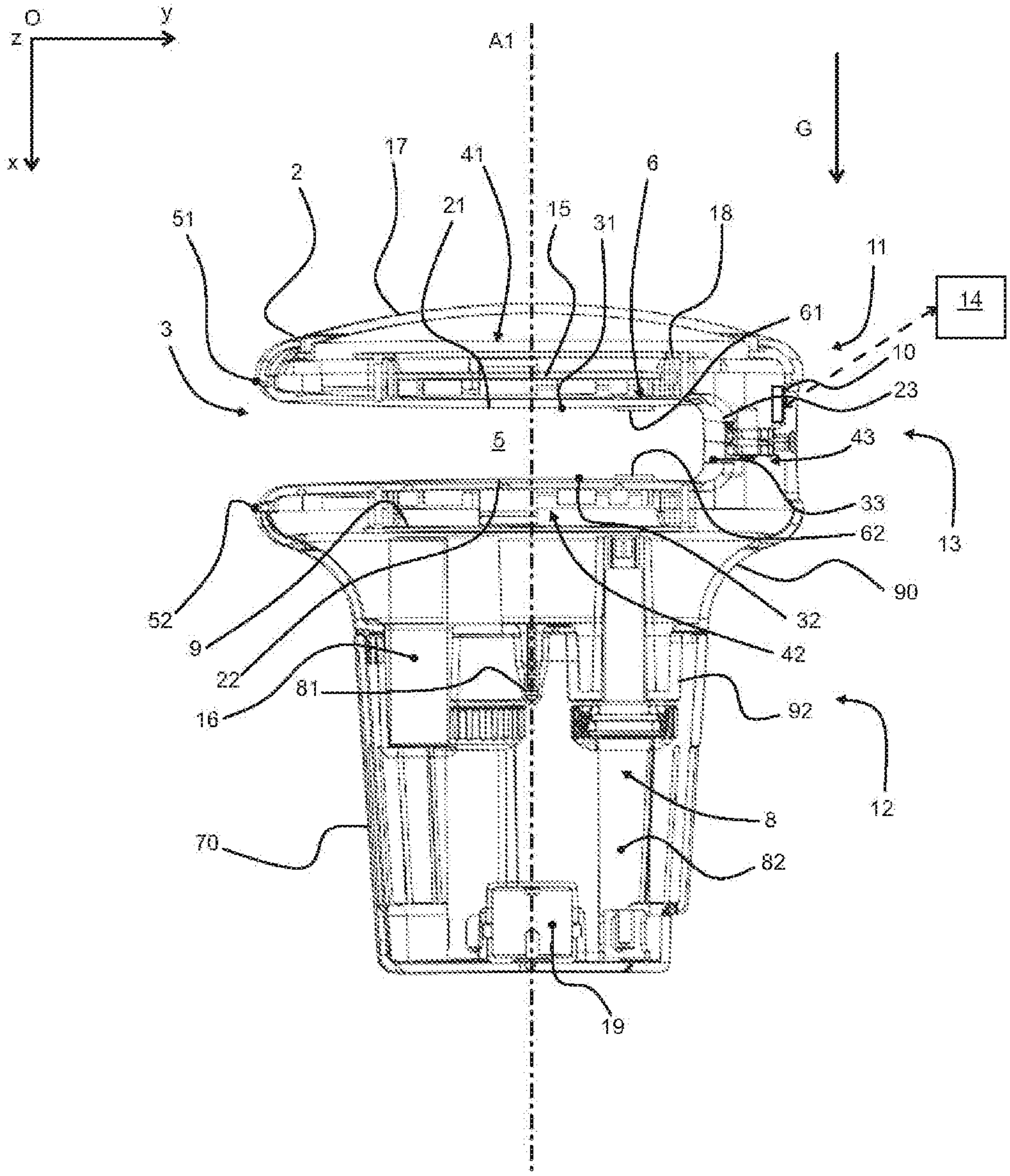

[Fig. 10]
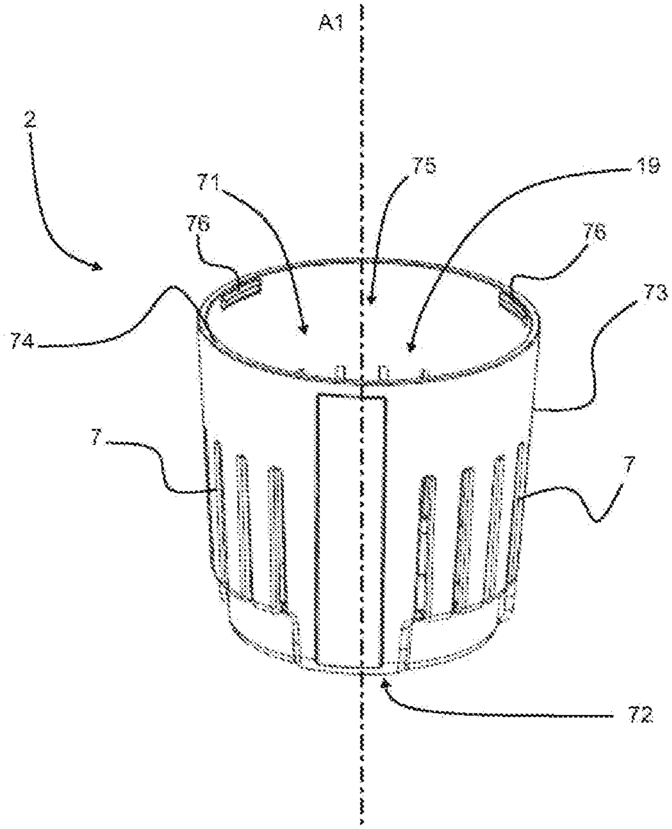

[Fig. 11]
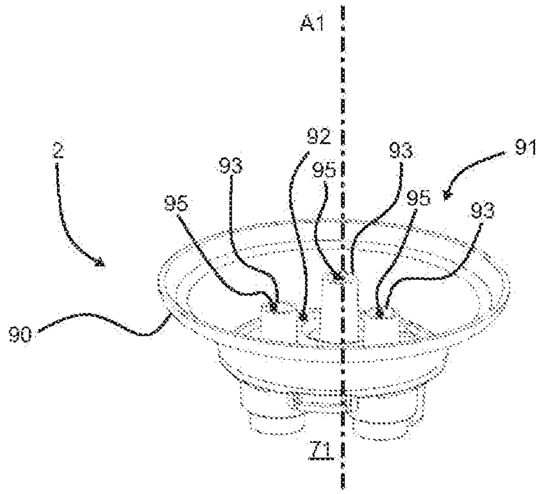

[Fig. 12]
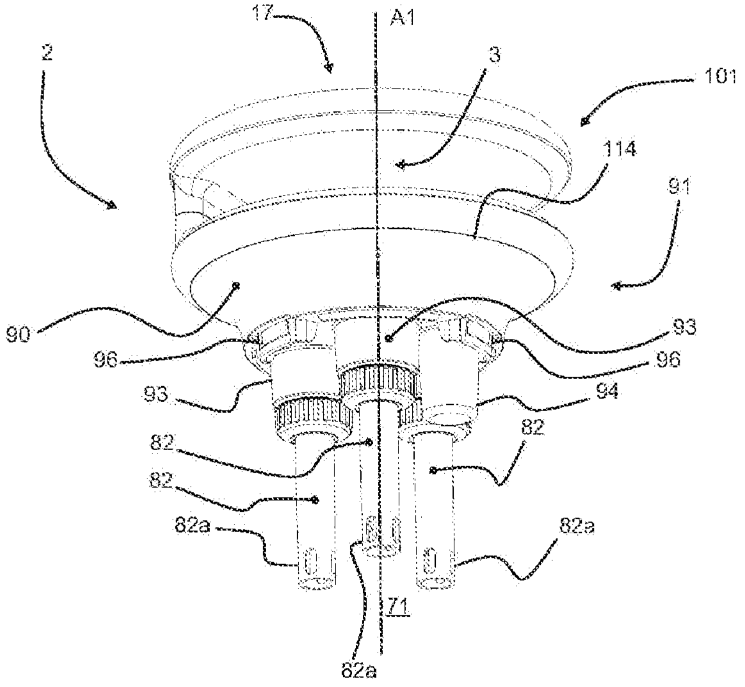

[Fig. 13]
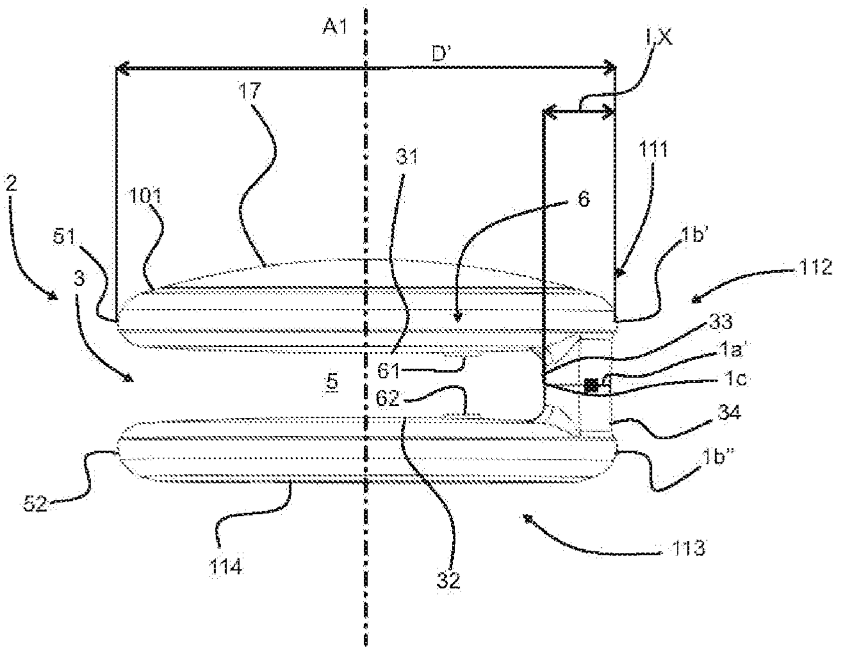

DEVICE FOR ANALYSING A LIQUID MEDIUM, IN PARTICULAR SWIMMING POOL WATER

The field of the present invention is that of devices for analyzing a liquid medium, in particular water of a swimming pool. It relates to such an analysis device. It also relates to an assembly comprising such an analysis device and a protective flap intended to float at the surface of the water of the swimming pool. It also relates to a swimming pool provided with such an assembly.

The document FR3064360 describes a device for analyzing a liquid medium comprising a body floating at the surface of a liquid medium, such as water of a swimming pool. The body comprises a sealed portion including a control unit of the analysis device connected to a communication module, a light source comprising at least two colors, an accelerometer and a database. The sealed portion is emerged and overhangs the surface of the water of the swimming pool. The sealed portion is generally spherical and comprises a photovoltaic cell allowing recharging a battery that the analysis device also comprises. The body also comprises an immersed portion comprising sensors for measuring quality characteristics of the liquid medium, such as the pH, the electrical conductivity, the temperature, the electro-reduction potential, the sensors being connected to the control unit. The emerged portion is generally cylindrical and includes a flared area that joins the spherical sealed portion.

Such an analysis device is intended in particular to analyze the water of a swimming pool provided with a protective flap. This protective flap is intended to prevent a fall of a person, in particular a child, into the swimming pool in order to avoid drowning of the latter. This protective flap is also intended to prevent dirt, tree leaves or the like, from falling into the water of the swimming pool and soiling it. This protective flap also enables thermal insulation of the water of the swimming pool, for example during a period of non-use of the swimming pool, which aims to minimize cooling of the water of the swimming pool.

To this end, the protective flap is movable between a covering position in which the protective flap covers the water of the swimming pool while floating at the surface of the latter and a stowage position in which the protective flap is wound around a storage axis located proximate to a rim of the swimming pool. The protective flap is commonly maneuvered between the stowage position and the covering position until one end of the protective flap comes into contact with the rim of the swimming pool.

A general problem in the field lies in the impossibility of using such an analysis device when the protective flap is maneuvered from the stowage position into the covering position. Indeed, the sealed portion, emerged, forms an obstacle to the movement of the protective flap until it is wedged between the end of the protective flap and the edge of the swimming pool. This results in a possibility of deformation, and even deterioration, of the protective flap and/or of the analysis device.

Another general problem in the field lies in the impossibility of using such an analysis device when the protective flap is placed in the covering position. Indeed, in the covering position of the protective flap, the analysis device risks being completely immersed. This results in a detrimental loading of sealing of the analysis device which should be perfect at the sealed portion. Yet, a prolonged stay in the water might cause an alteration of the sealing of the sealed portion on the long run. In addition, when the analysis device is immersed and covered by the protective flap, an operation of the communication module might be altered, and even stopped, the protective flap and/or the water forming a screen detrimental to the operation of the communication module. Still in addition, when the analysis device is immersed and covered by the protective flap, the photovoltaic cell no longer captures the light rays and therefore becomes unable to recharge the battery, which considerably reduces an autonomy of the analysis device.

One possibility is to remove the analysis device from the swimming pool when maneuvering the protective flap on the swimming pool. Yet, it is desirable to continuously have quality characteristics of the liquid medium, to avoid any drift of these and to rapidly adapt a treatment of the liquid medium, where necessary. Hence, this possibility turns out to be restrictive and ultimately unsatisfactory.

Another possibility is to leave the protective flap covering the analysis device and completely immerse the latter in the water of the swimming pool. As mentioned, this possibility results in malfunctions of the communication module, of the photovoltaic cell and alters sealing of the analysis device. Hence, this possibility is unsatisfactory.

Another possibility is to not fully deploy the protective flap when the analysis device is in place, which proves to be dangerous, a child might fall into the swimming pool in an interstice formed between the end of the protective flap and the rim of the swimming pool, the protective flap might then prevent the child from resurfacing and from getting out of the swimming pool. Hence, this possibility is to be discarded.

The present invention falls within this context and provides a device for analyzing a liquid medium, in particular swimming pool water. The analysis device comprises a casing housing means for analyzing the liquid medium for measuring physico-chemical parameters of the liquid medium, monitoring means for managing the measured parameters, communication means capable of transmitting said parameters to a central unit, at least one photovoltaic panel connected to electrical energy storage means for supplying electrical energy to the analysis means, the monitoring means and the communication means.

According to the present invention, the casing comprises a gripping member which is arranged in a U-like fashion and which delimits a space capable of receiving one end of a protective flap.

Advantageously, the analysis device comprises at least one of the following technical features, considered separately or in combination:

- the gripping member comprises a constituent first wall of a first sealed portion, a constituent second wall of a second immersed portion comprising a base provided with a plurality of apertures and housing the analysis means, and a third wall provided with a flap stop arranged so as to receive the end of the protective flap,
- the gripping member is provided with a means for detecting a presence of the protective flap inside the space, the detection means comprising a first detection member equipping the first wall and a second detection member equipping the second wall,
- the first wall borders a first chamber which houses the photovoltaic panel and which is overhung by a cover made of a translucent and phosphorescent material,
- the second wall borders a second chamber which houses the monitoring means and the electrical energy storage means, the second chamber being partially delimited by a sealing partition which forms a sealing cover and which seals an opening of the base,

- the sealing cover comprises a constituent peripheral flange of the casing, the peripheral flange being interposed between a cap of the analysis device and the base,
- the third wall borders a third chamber which houses the communication means,
- the third chamber is bordered by a fourth wall provided with a first anchoring member of the analysis device.

Another object of the present invention is an assembly comprising such an analysis device and the protective flap.

Another object of the present invention is a swimming pool equipped with such an assembly.

Other features and advantages of the invention will appear better through the following description, on the one hand, and from several embodiments given for non-limiting illustrative purposes with reference to the appended schematic drawings, on the other hand, wherein:

FIG. 1 is a schematic side illustration of a device for analyzing a liquid medium of the present invention, in a first position of use of the analysis device, wherein the analysis device is anchored against a rim of a swimming pool.

FIG. 2 is a schematic side illustration of the analysis device illustrated in FIG. 1, and shown in a second position of use of the analysis device, in which the analysis device is free-floating in the liquid medium.

FIG. 3 is a schematic side illustration of an assembly comprising the analysis device illustrated in FIGS. 1 and 2, and a protective flap during a movement between a stowage position and a covering position in which the protective flap covers the liquid medium.

FIG. 4 is a schematic top illustration of the assembly shown in FIG. 3, the protective flap being illustrated in the covering position.

FIG. 5 is a schematic top illustration of the assembly shown in FIGS. 3 and 4, the protective flap being illustrated in the stowage position.

FIG. 6 is a schematic side illustration of the assembly illustrated in FIGS. 3 to 5, the protective flap being illustrated in the covering position.

FIG. 7 is a schematic side illustration of the analysis device illustrated in FIGS. 1 and 2.

FIG. 8 is a schematic side illustration of the assembly illustrated in FIGS. 3 to 6.

FIG. 9 is a schematic sectional illustration of the analysis device illustrated in FIGS. 1, 2 and 7.

FIG. 10 is a schematic perspective illustration of a constituent base of the analysis device illustrated in FIGS. 1, 2, 7 and 9.

FIG. 11 is a schematic top perspective illustration of a constituent sealing cover of the analysis device illustrated in FIGS. 1, 2, 7 and 9.

FIG. 12 is a schematic bottom perspective illustration of the sealing cover illustrated in FIG. 11.

FIG. 13 is a schematic side illustration of a constituent cap of the analysis device illustrated in FIGS. 1, 2, 7 and 9.

In FIGS. 1 to 9, a device 1 for analyzing a liquid medium M of the present invention is shown inside an orthonormal reference frame Oxyz. The orthonormal reference frame Oxyz comprises an axis Ox which is a vertical axis, parallel to the terrestrial gravity axis G. The orthonormal reference frame Oxyz also comprises a plane Oyz which is a horizontal plane, orthogonal to the terrestrial gravity axis G.

In FIGS. 1 to 3, the analysis device 1 is intended to analyze the liquid medium M, such as the water of a swimming pool, a jacuzzi or the like. The analysis device 1 extends mainly according to an axis of elongation A1, which is parallel to the axis Ox, in positions of use of the analysis device 1 inside the liquid medium M, as shown in FIGS. 1 to 6. It should be noted that, in the position of use of the analysis device 1 inside the liquid medium M, the axis of elongation A1 is substantially orthogonal to a surface S of the liquid medium M, hereinafter referred to as the water.

In FIG. 1, the analysis device 1 is shown in a first position of use in which the analysis device 1 is anchored to a first rim R of the swimming pool via an anchoring means 1*a*. The anchoring means 1*a* is indifferently a magnetic, mechanical or similar anchoring means. The anchoring means 1*a* is shaped so that the anchoring is reversible. In other words, the anchoring means 1*a* allows either keeping the analysis device 1 in the first position of use against the first rim R of the swimming pool, as illustrated in FIG. 1, or leaving the analysis device 1 free-floating, as illustrated in FIG. 2. It should be understood that the anchoring means 1*a* is for example formed by a first anchoring member 1*a*' and a second anchoring member 1*a*", respectively assigned to the analysis device 1 and to the first rim R of the swimming pool. For example, the anchoring members 1*a*', 1*a*" are formed of a pair of magnets, a loop and a hook, or the like, which are formed at the surface S of the water.

It should also be noted that the analysis device 1 comprises at least one device stop 1*b*', 1*b*", and preferably two device stops 1*b*', 1*b*", which are shaped so as to come into contact with the first rim R of the swimming pool, for example from a thickened portion of material of the analysis device 1.

FIG. 3 shows an assembly 100 comprising the analysis device 1 and a protective flap 4 for the water of the swimming pool. In general terms, the protective flap 4 is movable between a covering position, illustrated in FIG. 4, in which the protective flap 4 covers the water of the swimming pool by floating at the surface S of the latter and a stowage position, illustrated in FIG. 5, in which, for example, the protective flap 4 is wound around a storage axis A2 located close to a second rim R' of the swimming pool, in particular located opposite the first rim R of the swimming pool equipped with the second anchoring member 1*a*", as illustrated in FIG. 5. Preferably, the protective flap 4 is formed of slats 4*b* which are connected in pairs by a hinge means 4*c*. In other words, the protective flap 4 is intended to undergo a movement D between the stowage position and the covering position until one end 4*a* of the protective flap 4 comes into contact with a flap stop 1*c* of the analysis device 1, such that the analysis device 1 is blocked between the end 4*a* of the protective flap 4 and the rim R of the swimming pool, as illustrated in FIG. 6.

It should be noted that a distance X considered orthogonally to the axis of elongation A1 between the flap stop 1*c* and one of the device stops 1*b*', 1*b*" is as reduced as possible, in particular in the range of few centimeters, such that an interstice I considered orthogonally to the axis of elongation A1 between the flap end 4*a* and the rim R of the swimming pool is also as reduced as possible, the interstice I and the distance X being substantially equivalent to each other. It should be noted that the interstice I and/or the distance X are in particular less than 25%, and possibly and preferably 10%, of a dimension D' of the analysis device 1 considered in a plane substantially orthogonal to the axis of elongation A1. For example, the dimension D' is a diameter of the generally cylindrical analysis device 1 whose axis of elongation A1 forms an axis of revolution.

This advantageous arrangement is achieved from a particular arrangement of the analysis device 1 described hereinafter.

In FIGS. 7 and 8, the analysis device 1 comprises a first portion 11, in particular higher in the position of use of the analysis device 1, and a second portion 12, in particular lower in the position of use of the analysis device 1, which are connected to one another by an intermediate portion 13. It should be understood that the intermediate portion 13 is interposed between the first portion 11 and the second portion 12 and that, in the position of use, the first portion 11 overhangs the second portion 12 and the intermediate portion 13. In other words, when covering the axis of elongation A1, one could successively find the first portion 11, the intermediate portion 13, and then the second portion 12. The first portion 11 is a sealed part intended to emerge above the surface S of the water whereas the second portion 12 is intended to be immersed inside the water of the swimming pool, as illustrated in FIG. 4.

It should also be understood that the first portion 11 overhangs the protective flap 4 in the covering position, as illustrated in FIG. 4.

The analysis device 1 comprises a casing 2 which delimits the first portion 11, the second portion 12 and the third portion 13. The casing 2 forms an outer surface of the analysis device 1 visible from outside the latter. Advantageously, the casing 2 includes a gripping member 3 which is able to grip the protective flap 4 of the swimming pool, as shown in FIGS. 4, 6 and 8.

It should be understood that the gripping member 3 is shaped to wrap around the protective flap 4. In other words, the gripping member 3 is arranged such that the protective flap 4 can fit inside the gripping member 3, until the end 4*a* of the protective flap 4 comes into contact against the flap stop 1*c* of the analysis device 1. To this end, the gripping member 3 is arranged in a U-like fashion, a first branch 21 of which forms the first portion 11, a second branch 22 of which forms the second portion 12 and a base 23 of which forms the intermediate portion 13. Thus, the gripping member 3 comprises a first wall 31 which forms the first branch 21 of the U and which partially delimits a first chamber 41 of the first portion 11. The gripping member 3 also comprises a second wall 32 which forms the second branch 22 of the U and which partially delimits a second chamber 42 of the second portion 12. The gripping member 3 also comprises a third wall 33 which forms the base 23 of the U and which delimits a third chamber 43 of the intermediate portion 13. Advantageously, the third wall 33 includes the flap stop 1*c* of the analysis device 1. The first wall 21 extends mainly according to a first plane P1 which is orthogonal to the axis of elongation A1, the second wall 22 extends mainly inside a second plane P2, distinct from and parallel to the first plane P1 whereas the third wall 23 extends substantially inside a third plane P3 orthogonal to the first plane P1 and to the second plane P2.

The first branch 21 comprises a first end 51, opposite to the base 23, which is arranged in a guide ramp of the protective flap 4 to facilitate insertion of the latter inside the gripping member 3. Similarly, the second branch 22 comprises a second end 52, opposite to the base 23, which is arranged in a guide ramp of the protective flap 4 to facilitate insertion of the latter inside the gripping member 3.

The gripping member 3 is provided with a means 6 for detecting a presence of the protective flap 4 inside a space 5 delimited by the gripping member 3 and bordered by the first wall 31, the second wall 32 and the third wall 33. The detection means 6 comprises a first detection member 61 equipping the first wall 31 and a second detection member 62 equipping the second wall 32. The detection means 6 is indifferently an optical, inductive, capacitive or similar detection means.

The second portion 12 is provided with a plurality of apertures 7 formed through the casing 2 such that the water can penetrate inside the second portion 12 in order to be analyzed by analysis means 8 housed in the second portion. According to one variant, the apertures 7 are circular. According to the illustrated variant, the apertures 7 are oblong.

In FIG. 9, the analysis means 8 comprise a temperature sensor 81 for measuring a temperature of the water and of the electrodes 82 for measuring physico-chemical parameters of the water, such as the pH, the oxidation-reduction potential, the electrical conductivity, the salinity ratio or the like. The analysis means 8 are connected to monitoring means 9 which are able to manage said parameters measured by the temperature sensor 81 and the electrodes 82. The monitoring means 9 are connected to communication means 10, such as a radiofrequency antenna, a Wi-Fi antenna or the like, which are able to transmit said parameters to a central unit 14 located remotely from the analysis device, for example in a technical room. Advantageously, the communication means 10 are housed inside the third chamber 43.

The analysis means 8 are also connected to a photovoltaic panel 15, housed in the first chamber 41, which is able to transform light rays into an electrical energy intended to be stored in electrical energy storage means 16, such as a battery or the like. For example, the photovoltaic panel 15 extends inside a plane orthogonal to the axis of elongation A1.

The casing 2 comprises a cover 17 which is made of a translucent and phosphorescent material in order to let the light rays pass towards the photovoltaic panel 15. To this end, the cover 17 overhangs the photovoltaic panel 15 which also overhangs at least one light-emitting diode 18, and preferably a plurality of RGB RGBW light-emitting diodes which, through the combination of their activation by the monitoring means 9, allows changing the color of the cover 17 in a variation in hue. Depending on the colors of the cover 17 and/or their blinking mode, a user is informed on an operating state of the analysis device 1, and possibly on the result of the parameters measured by the temperature sensor 81 and the electrodes 82, and in particular on a crossing of a threshold parameter for any one of these parameters. The cover 17 includes colored photoluminescent pigments which accumulate light energy during the day and renders it overnight, thereby enabling the analysis device 1 to be illuminated without consuming electrical energy.

The second portion 12 houses a ballast 19 for placing the analysis device 1 in the position of use, such as that one defined hereinabove.

In FIG. 10, the casing 2 comprises a base 70 arranged into a cuvette which delimits an enclosure 71 shaped so as to house the ballast 19 and provided with the apertures 7. The base 70 includes a bottom 72 and a cylindrical, or substantially cylindrical, wall 73, which extends between the bottom 72 and a circular rim 74, the circular rim 74 delimiting an opening 75. The bottom 72 is equipped with the ballast 19 whereas the cylindrical wall 73 is provided with the apertures 7. The bottom 72 extends in a plane orthogonal to the axis of elongation A1, the cylindrical wall 73 includes an axis of symmetry coincident with the axis of elongation A1 and the circular rim 74 extends in a plane orthogonal to the axis of elongation A1. Advantageously, the base 70 houses the analysis means 8.

In FIGS. 11 and 12, the casing 2 comprises a peripheral collar 90 which forms a sealing cover 91. More particularly, the sealing cover 91 comprises the peripheral collar 90 which belongs to the casing 2 and a sealing partition 92 which is bordered by the peripheral collar 90 which forms a bottom thereof. The sealing partition 92 is intended to seal the opening 75 so that the enclosure 71 forms a chamber for analyzing the water tightly isolated from the rest of the analysis device 1. The sealing partition 92 is provided with barrels 93 for receiving the electrodes 82 an electrode end 82*a* of which is immersed in the enclosure 71. The sealing partition 92 is also provided with a box 94 for receiving the electrical energy storage means 16. The sealing partition 92 is formed in a plane which is orthogonal to the axis of elongation A1, the peripheral flange 90 includes an axis of symmetry which is coincident with the axis of elongation A1. Each of the receiving barrels 93 and the receiving box 94 includes an axis of symmetry which is parallel to the axis of elongation A1. It should be noted that the receiving box 94 is blind to guarantee sealing with respect to the enclosure 71 whereas the receiving barrels 93 delimit an open-through passage 95. The sealing cover 91 includes interlocking tabs 96 which cooperate with interlocking fingers 76 that the cylindrical wall 73 comprises to enable assembly of the base 70 and of the peripheral collar 90.

In FIG. 13, the casing 2 comprises a cap 101 generally U-shaped and provided with the gripping member 3. The cap 101 comprises an upper element 111 forming a branch of the U, a lower element 112 forming the other branch of the U and an intermediate element 113 forming the base of the U. The upper element 111 includes the cover 17, the first guide ramp 51 which forms one end of the U, the first device stop 1*b*', the first wall 31 and the first detection member 61. The lower element 112 includes a base 114 axially opposite to the cover and through which the cap 101 is attached on the sealing cover 91, as illustrated in FIG. 12. The lower element 112 also includes the second guide ramp 52 which forms the other end of the U, the second device stop 1*b*", the second wall 32 and the second detection member 62. It should be noted at this stage of the description that the dimension D' is for example the distance considered orthogonally to the axis of elongation A1 between the first guide ramp 51 and the first device stop 1*b*', or else the distance considered orthogonally to the axis of elongation A1 between the second guide ramp 52 and the second device stop 1*b*".

The intermediate element 113 includes the third wall 33 provided with the flap stop 1*c* and a fourth wall 34, radially opposite to the third wall 33, which is provided with the first anchoring member 1*a*'.

The result of all these arrangements is that the present invention advantageously provides a device 1 for analyzing a liquid medium capable of measuring the physico-chemical parameters of the liquid medium, irrespective of the position of the protective flap 4, in particular placed in the covering position, the analysis device 1 being capable of transmitting said parameters to the central unit 14 to adapt a treatment of the liquid medium where necessary, such a treatment taking in particular account of the position of the protective flap 4 detected by the detection means 6, the analysis device 1 being autonomous because of the presence of the photovoltaic panel 15 with respect to the electrical energy storage means 16 to supply electrical energy to the analysis means 8, the monitoring means 9 and the communication means 10, the analysis device 1 comprising the gripping member 3 which is arranged in a U-like fashion so as to delimit the space 5 able to receive the end 4*a* of the protective flap 4, the gripping member being equipped with means 6 for detecting the position of the protective flap 4 inside the space 5, such a U-shaped arrangement of the gripping member 3 being such that the distance X between the flap stop 1*c* and one of the device stops 1*b*', 1*b*" is as reduced as possible, in particular less than 25%, and possibly 10%, of said dimension D', in particular in the range of a few centimeters, such that the interstice I between the flap end 4*a* and the rim R of the swimming pool is as reduced as possible also, so that in the covering position, the protective flap 4 prevents swimming and protects the liquid medium from solar radiations, thereby significantly reducing a need for disinfectant products in the swimming pool. It should then be understood that the position of the protective flap 4 is an important piece of information for the automatic treatment of the water of the swimming pool.

The invention claimed is:

1. A device for analyzing a liquid medium, the device comprising:
- an analyzer adapted to analyze the liquid medium so as to measure physico-chemical parameters of the liquid medium;
- a casing having a gripping member of a U-shape, said casing defining a space that receives one end of a protective flap, wherein the gripping member has a first wall with a sealed portion and a second wall with an immersed portion and a third wall having a flap stop receiving the one end of the protective flap, the immersed portion having a base with a plurality of apertures and a housing receiving said analyzer;
- a monitor adapted to manage the measured physico-chemical parameters from said analyzer;
- a transmitter connected to said analyzer so as to transmit the measured physico- chemical parameters to a control unit; and
- at least one photovoltaic panel connected to an energy storage device, the energy storage device connected to said analyzer and to said monitor and to said transmitter so as to supply energy to said analyzer and to said monitor and to said transmitter.

2. The device of claim 1, wherein the gripping member has a detector detects a presence of the protective flap inside the space, the detector having a first detection member on the first wall and a second detection member on the second wall.

3. The device of claim 1, wherein the first wall borders a first chamber that houses said at least one photovoltaic panel, the first chamber being overhung by a cover, the cover being formed of a translucent and phosphorescent material.

4. The device of claim 3, wherein the second wall borders a second chamber that houses the monitor and the energy storage device, the second chamber being partially defined by a sealing partition which forms a sealing cover and which seals an opening of the base.

5. The device of claim 4, wherein the sealing cover has a peripheral flange of said casing, the peripheral flange being interposed between a cap of said analyzer and the base.

6. The device of claim 1, wherein the third wall borders a third chamber, the third chamber housing said transmitter.

7. The device of claim 6, wherein the third chamber is bordered by a fourth wall, the fourth wall having an anchor for said analyzer.

8. An assembly comprising the device of claim 1.

9. A swimming pool equipped with the assembly of claim 8.

* * * * *